United States Patent [19]

Radons et al.

[11] Patent Number: 5,487,751
[45] Date of Patent: Jan. 30, 1996

[54] MECHANICAL CONNECTOR FOR SECURING COMPATIBLE MEDICAL INSTRUMENTS TOGETHER

[75] Inventors: Stephen W. Radons, Snohomish; Steven L. King, Kirkland; Randall D. Mills, Woodinville; Cliff Cristobal, Kirkland, all of Wash.

[73] Assignee: Physio-Control Corporation, Redmond, Wash.

[21] Appl. No.: 334,624

[22] Filed: Nov. 4, 1994

[51] Int. Cl.$^6$ ..................................... A61B 19/02
[52] U.S. Cl. .................... 607/1; 607/2; 128/897
[58] Field of Search ................... 607/36, 5, 2, 1; 439/909; 128/897

[56] References Cited

U.S. PATENT DOCUMENTS 4,096,856  6/1978  Smith et al. .................. 128/4.19 D Primary Examiner—George Manuel
Assistant Examiner—Kennedy J. Schaetzle
Attorney, Agent, or Firm—Christensen, O'Connor Johnson & Kindness

[57] ABSTRACT

A mechanical connector (10) for securing together an electrocardiogram monitor (12) and a defibrillator (14). The connector includes a tongue (16) disposed on a side surface (18) of the ECG monitor and a set of angle flanges (22) disposed on the defibrillator. A keyway (52) extends lengthwise at a rearward portion of a channel (36) between the tongue (16) and the side surface (18). A key (50) fits within the keyway (52) when the tongue (16) is slid within the set of angle flanges (22). The key (50) prevents the defibrillator from being fully coupled with an ECG monitor that lacks the corresponding keyway.

2 Claims, 3 Drawing Sheets

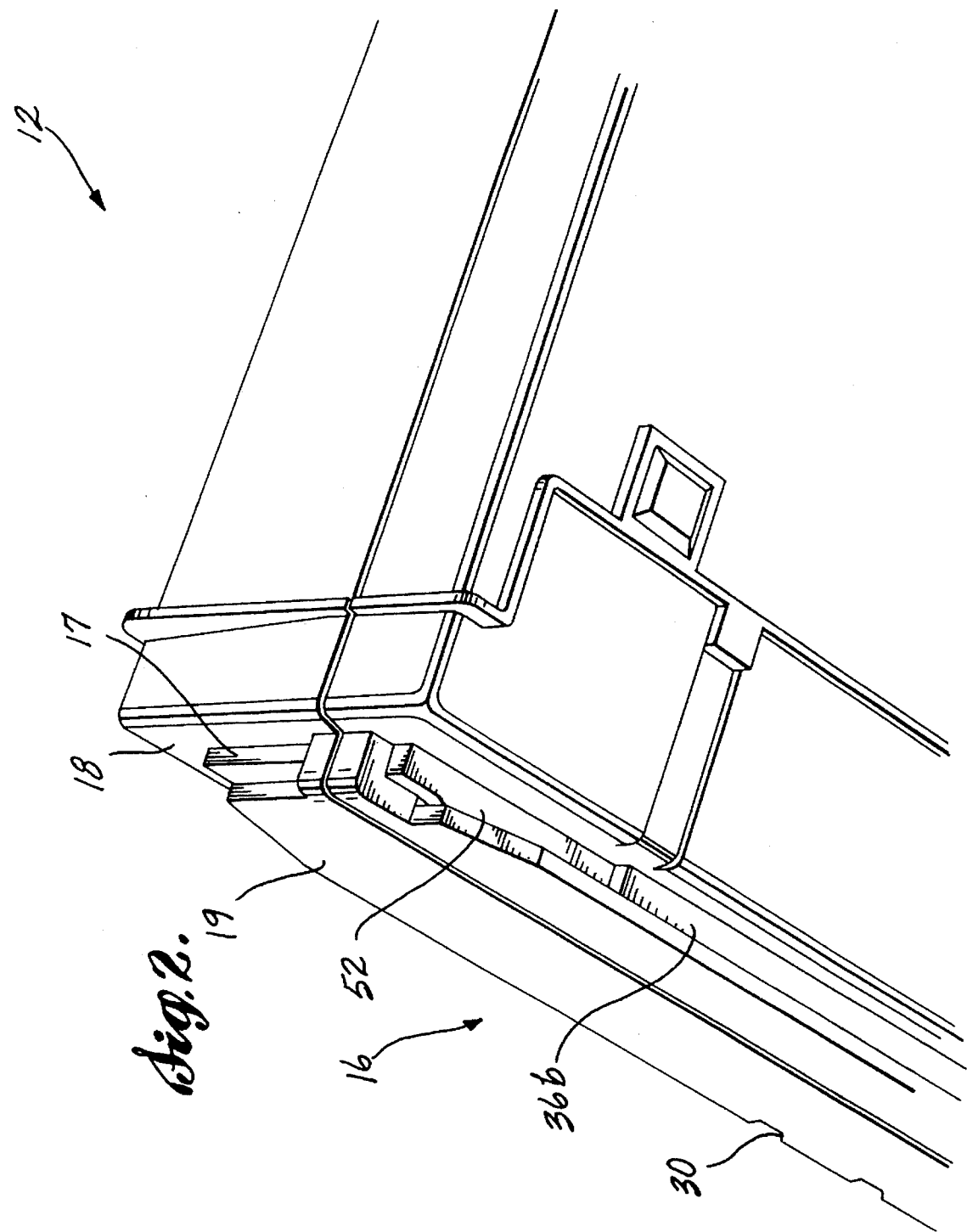

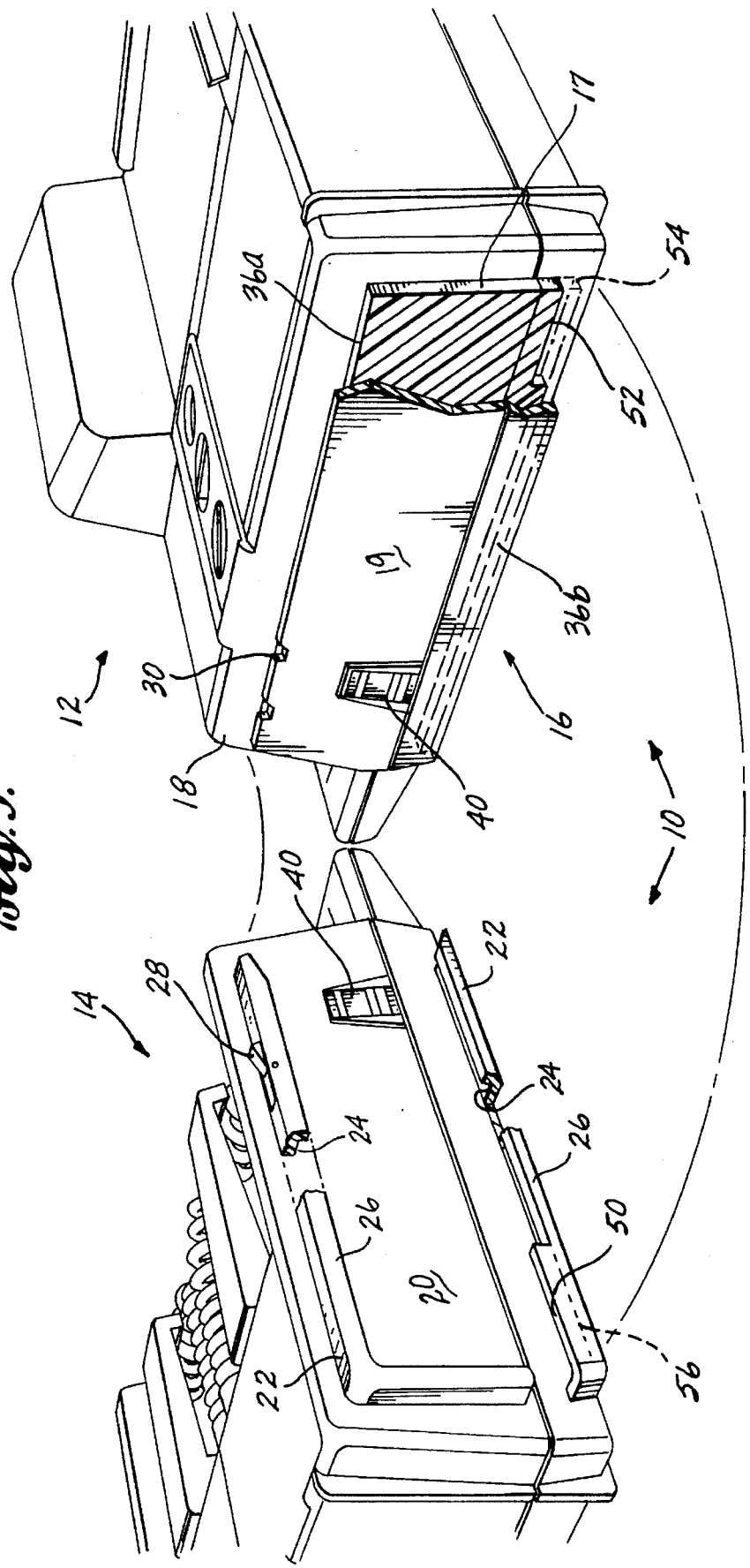

5,487,751

MECHANICAL CONNECTOR FOR SECURING COMPATIBLE MEDICAL INSTRUMENTS TOGETHER

FIELD OF THE INVENTION

The present invention relates to mechanical connectors in general, and in particular to mechanical connectors for securing together compatible medical instruments.

BACKGROUND OF THE INVENTION

Many modern medical instruments are comprised of two or more stand-alone components that perform specialized functions. The components may be used alone only if a single function is desired, or the components may be coupled together to form a medical instrument having multifunction capabilities. One example of a multicomponent medical instrument is the LIFEPAK 5® electrocardiogram monitor and defibrillator produced by Physio-Control Corporation of R. edmond, Washington. The monitor records and analyzes a patient's electrocardiogram (ECG) signal while the defibrillator produces a high energy defibrillation pulse to terminate ventricular or atrial fibrillation. Each component may be used separately when only one function is desired. Alternatively, the monitor and defibrillator can be secured together as a single unit having both monitoring and defibrillation capability.

Mechanical connectors are typically used to secure the separate medical components together. One example of such a mechanical connector is disclosed in U.S. Pat. No. 4,096, 856 which is expressly incorporated by reference herein. Although the connector shown in the '856 patent was an improvement to the prior art, the connector was not designed to prevent the coupling of similar but incompatible medical instruments. During emergency situations, it is important that physicians or medical technicians not be able to connect and attempt to operate medical instruments that were not designed to work with each other.

SUMMARY OF THE INVENTION

The present invention is a mechanical connector for securing together a pair of compatible medical instruments such as an electrocardiogram monitor and a defibfillator. The connector includes a tongue on one of the medical instruments and a corresponding groove on the other of the medical instruments. A keyway extends lengthwise along a rearward portion of the tongue. A key within the groove fits the keyway when the medical instruments are secured together. The cooperating key and keyway are provided on compatible components, and prevent incompatible medical components from being coupled together.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2 is a bottom perspective of a keyway disposed within a tongue portion of the improved mechanical connector according to the present invention; and FIG. 3 is a rear perspective of the instruments of FIG. 1 with parts broken away, showing the interaction of a key and keyway to secure the medical instruments together.

DETAILED DESCRIPTION OF THE PREFERRED EMBODIMENT

Figure 1:
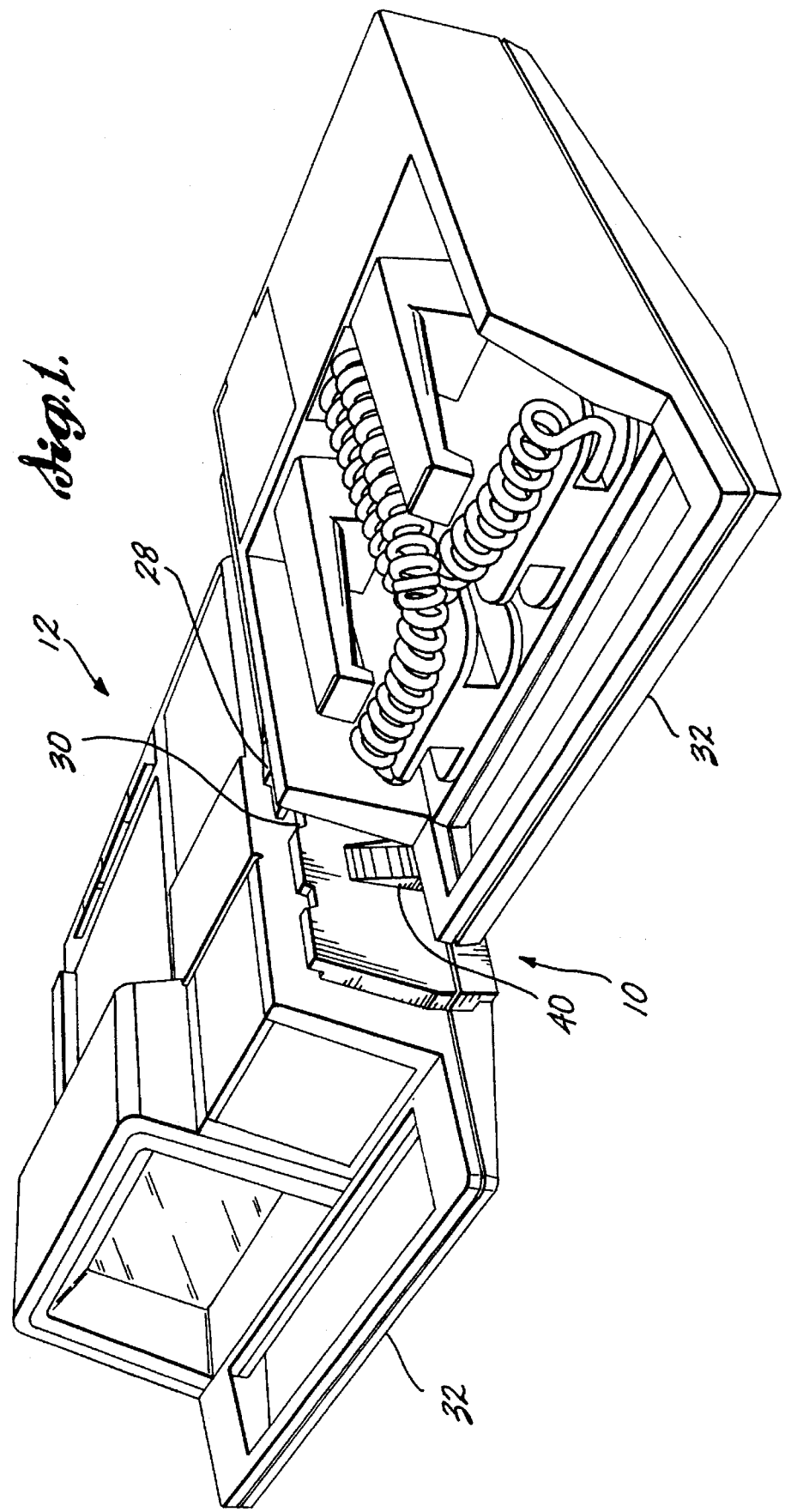
FIG. 1 is a top perspective of a pair of interconnectable medical instruments including an improved mechanical connector according to the present invention for securing the medical instruments together.

With reference to FIG. 1, the connector 10 in accordance with the present invention secures an electrocardiogram (ECG) monitor 12 to a defibrillator 14. When connected together, preferably the monitor and defibfillator are capable of serial data transfer by way of interengaged electrical contacts, as described in the copending application titled "Communication Interface for Transmitting and Receiving Serial Data Between Medical Instruments" by C. Johansen et al. (Attorney reference No. PHYS17974) commonly assigned with this application and filed concurrently herewith. Such application is expressly incorporated by reference herein. However, as described in such copending application, the monitor 12 having serial data transfer capability is also compatible with a less sophisticated defibrillator, namely, the LIFEPAK 5® defibfillator. Nevertheless, the more sophisticated defibfillator 14 (to be known as the LIFEPAK 11™ defibrillator) is not compatible with the less sophisticated monitor of the LIFEPAK 5® instrument. Therefore, to permit assembly of compatible components while preventing inadvertent assembly of incompatible components, the connector of the present invention permits the connection of a new LIFEPAK 11™ monitor with either a LIFEPAK 5® or a LIFEPAK 11™ defibrillator, but prevents the interconnection of a LIFEPAK 5® monitor with a LIFEPAK 11™ defibrillator.

The improved connector 10 has cooperating parts disposed on adjacent surfaces of the ECG monitor 12 and defibrillator 14. When the ECG monitor is coupled with the defibrillator, an electrical interface 40 on the monitor is brought into contact with the corresponding interface on the defibrillator to allow the serial data communication to take place between the two units. The data communication may involve the transmission of commands entered at one instrument to the other instrument, the transmission of status information regarding the operating condition of one of the instruments, or the transmission of physiological data sensed by one of the instruments. It is important that the interfaces engage reliably and precisely to allow the communication to take place. It is equally important that interfaces of incompatible components not be engaged. Otherwise, the internal circuitry could be damaged or valuable time could be lost if the source of one or both units failing to operate as intended is not immediately discovered.

Consequently, the connector 10 is designed so that only compatible medical instruments can be connected to the ECG monitor 12. In addition to communication protocol, compatibility may be based on the electrical characteristics of the instruments or the features provided by the instrument. For example, it does not typically make sense to connect two ECG monitors together. Therefore, an ECG monitor is said to be incompatible with another ECG monitor. If a medical instrument is not compatible, the connector 10 -will not allow the incompatible medical instrument to become fully engaged with ECG monitor 12. By preventing the full engagement of an incompatible medical instrument, the electrical interface on each instrument cannot engage and data communication cannot take place. The nature of the improved connector 10 makes this immediately apparent to the technician.

Turning now to FIG. 3, the connector 10 includes a tongue portion 16 spaced outward from a side face 18 of the ECG monitor 12. The tongue section 16 includes a joining section 17 that is flush with the side face 18 of the ECG monitor 12. An outer wall 19 is positioned over the joining section 17. The outer wall 19 of the tongue is wider than the joining section 17 such that the top and bottom portions overhang the joining section. The space between the side face 18 and the overhanging portions of the outer wall 19 creates a top channel 36a and a bottom channel 36b. The top channel 36a is of a substantially uniform depth along its entire length. An opposing face 20 of the defibrillator 14 includes angle flanges 22 forming top and bottom channels or grooves 24 that mate with the top and bottom portions of the tongue 16. Each groove 24 opens toward the horizontal center of the defibrillator and is bounded at the outside by a leg 26 of the corresponding flange 22. Legs 26 are spaced outward from the defibrillator side face 20. The top and bottom portions of the tongue 16 fit between the defibrillator side face 20 and legs 26 to secure the defibrillator to the ECG monitor. More specifically, with the tongue 16 registered with the grooves 24, the defibrillator is translated from the rear of the monitor toward the front, as illustrated in FIG. 1, until the two units are in the desired alignment. When the defibrillator is fully engaged with the ECG monitor, the electrical interfaces 40 on the ECG monitor and defibrillator are engaged so that data communication can take place between the two units. Additionally, a latch 28 on the defibrillator can be interengaged with a notch 30 on the monitor tongue to prevent the components from separating when carried by their front handles 32.

As indicated above, the connector 10 according to the present invention prevents incompatible components from being secured together. This is accomplished through the use of a key 50 and corresponding keyway 52 provided only on the LIFEPAK 11™ defibrillator and monitor respectively. As best seen in FIG. 2, the tongue 16 of the connector forms a shallow, downward opening channel 36b. The channel 36b has a substantially uniform depth along its length. However, a rear portion of the channel is cut deeper to create the keyway 52. Keyway 52 extends from the rear end of the tongue forward for a distance of about two inches.

As can be seen in FIG. 3, on the defibrillator, the bottom angle flange 22 is formed with a vertical leg wider (i.e., higher) at its rear end portion than its forward portion. The wider rear end portion forms the key 50 of a length approximately equal to the length of the keyway 52. Similarly, the height of the key is approximately equal to the depth of the keyway. Thus, when the monitor 12 and defibrillator 14 are interengaged, the key 50 fits closely in the keyway 52.

In the prior art LIFEPAK 5®, however, there is no corresponding key and keyway. Rather, the depth of the bottom channel formed by the tongue is consistent from the front to the back of the tongue, as indicated by the broken lines 54 shown in FIG. 3. On the LIFEPAX 5® defibrillator, the height of the bottom leg 26 is substantially uniform from the front to the back, as indicated by the broken lines 56. The result is that a LIFEPAK 5® defibrillator can be easily coupled with either a LIFEPAK 5® monitor or a LIFEPAK 11™ monitor. In the case of a LIFEPAK 11™ monitor, the keyway 52 simply forms an empty notch above the bottom angle flange on the LIFEPAK 5® defibrillator. However, if a technician tries to couple a LIFEPAK 11™ defibrillator with a LIFEPAK 5® monitor, the defibrillator key 50 will butt against the rear of the tongue body before the instruments are fully coupled. Thus, different defibrillators, both of which are compatible with the LIFEPAK 11™ can be coupled to the LIFEPAK 11™ monitor of the present invention, whereas the LIFEPAK 11™ defibrillator of the present invention is prevented from being connected to the LIFEPAK 5® monitor.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A mechanical connector for securing a first and a second medical instrument together, wherein said first and second medical instruments include an electrical interface through which data can be transmitted from the first instrument to the second instrument, the connector comprising:

a tongue portion disposed on the first instrument, the tongue portion including a joining section disposed on a side wall of the first instrument and an outer wall disposed on the joining section, the outer wall having a width that is wider than the joining section to create a top and a bottom channel between the outer wall and the side wall of the first instrument, the top channel having a substantially uniform depth along its entire length and the bottom channel having a first depth along a major portion of its length and a second depth that is deeper than the first depth at a rearward portion of the bottom channel, said deep portion of the bottom channel defining a keyway;

a groove portion disposed on a side wall of the second instrument, the groove portion including a pair of angle flanges extending from the side wall of the second instrument, said groove portion being capable of receiving said outer wall of the tongue portion such that the electrical interfaces of the first and second instruments are engaged.

2. The mechanical connection of claim 1, wherein said groove portion includes an outer side wall, said outer side wall having a first section of substantially uniform height and a second section having a height that is greater than the height of the first section, the second section defining a key that fits within the keyway.

* * * * *